ary Examiner—Robert Gerstl

United States Patent [19]
White

[11] 4,450,161
[45] May 22, 1984

[54] PYRIMIDONE SALT AND ITS PREPARATION

[75] Inventor: George R. White, Harpenden, England

[73] Assignee: Smith Kline & French Laboratories Limited, Welwyn Garden City, England

[21] Appl. No.: 382,027

[22] Filed: May 26, 1982

[51] Int. Cl.$^3$ .................. C07D 403/12; A61K 31/505
[52] U.S. Cl. ..................................... 424/251; 544/321
[58] Field of Search ................. 544/319, 321; 424/251

[56] References Cited

U.S. PATENT DOCUMENTS 4,352,933 10/1982 Lam ..................................... 544/320

Primary Examiner—Robert Gerstl
Attorney, Agent, or Firm—Joan S. Keps; Richard D. Foggio; Alan D. Lourie

[57] ABSTRACT

The invention provides 2-[2-(5-methyl-4-imidazolylmethylthio)ethylamino]-5-[5-(1,3-benzodioxolyl)methyl]-4-pyrimidone di(methanesulphonate) which is useful as a histamine $H_2$-antagonist. The compound can be prepared by reacting 2-[2-(5-methyl-4-imidazolylmethylthio)ethylamino]-5-[5-(1,3-benzodioxolyl)methyl]-4-pyrimidone with methanesulphonic acid.

7 Claims, No Drawings

PYRIMIDONE SALT AND ITS PREPARATION

This invention relates to 2-[2-(5-methyl-4-imidazolylmethylthio)ethylamino]-5-[5-(1,3-benzodioxolyl)-methyl]-4-pyrimidone di(methanesulphonate), pharmaceutical compositions containing it and methods of blocking histamine $H_2$-receptors by administering it.

U.S. Pat. No. 4,218,452 describes a class of 4-pyrimidones and their pharmaceutically acceptable acid addition salts which are useful as histamine $H_2$-receptor antagonists. For example addition salts are described with hydrochloric, hydrobromic, hydriodic, sulphuric and maleic acids. 2-[2-(5-Methyl-4-imidazolylmethylthio)-ethylamino]-5-[5-(1,3-benzodioxolyl)-methyl]-4-pyrimidone and the dihydrochloride salt of this compound are specifically described.

According to the present invention there is provided 2-[2-(5-methyl-4-imidazolylmethylthio)ethylamino]-5-[5-(1,3-benzodioxolyl)methyl]-4-pyrimidone di(methanesulphonate) which has histamine $H_2$-antagonist activity.

The dimethanesulphonate salt of the present invention has a number of advantages. Firstly it is a stoichiometric salt which can be easily recrystallized. Secondly it forms aqueous solutions which are relatively stable. For example aqueous solutions can be prepared containing at least 10% w/v of the salt (calculated as the free base) which do not crystallise out on being left to stand for up to 4 weeks at temperatures of 10°-25° C. In contrast, when 10% w/v aqueous solutions of the dihydrochloride salt described in U.S. Pat. No. 4,218,452 are left to stand at temperatures of 10°-25° C., a crystalline deposit forms after a relatively short time. These properties are of value since parenteral administration requires stable solutions which may contain at least 10% w/v of the salt.

2-[2-(5-Methyl-4-imidazolylmethylthio)ethylamino]-5-[5-(1,3-benzodioxolyl)methyl]-4-pyrimidone-di(methanesulphonate) can be prepared by reacting 2-[2-(5-methyl-4-imidazolylmethylthio)ethylamino]-5-[5-(1,3-benzodioxolyl)-methyl]-4-pyrimidone with methanesulphonic acid.

In general approximately two molar equivalents of acid will be used. The reaction is conveniently effected in aqueous solution, usually at an elevated temperature, for example at above 50° C. The di(methanesulphonate) salt can be isolated and purified by known methods, for example by evaporation and crystallisation, e.g. from a ($C_1$-$C_4$) alkanol. 2-[2-(5-Methyl-4-imidazolylmethylthio)ethylamino]-5-[5-(1,3-benzodioxolyl)methyl]-4-pyrimidone can be prepared from an acid addition salt by reacting the salt with a base using known methods.

The invention further provides a pharmaceutical composition comprising 2-[2-(5-methyl-4-imidazolylmethylthio)ethylamino]-5-[5-(1,3-benzodioxolyl)methyl]-4-pyrimidone di(methanesulphonate) and a pharmaceutically acceptable carrier.

Preferably the compositions are suitable for parenteral administration. Preferably the carrier is sterile pyrogen-free water. Preferably the compositions are aqueous solutions of 2-[2-(5-methyl-4-imidazolylmethylthio)ethylamino]-5-[5-(1,3-benzodioxolyl)methyl]-4-pyrimidone di(methanesulphonate) containing up to 5, 7.5 or 10% w/v of the salt calculated as the free base.

Preferably the compositions are in unit dosage form, for example ampoules or multi-dose vials, and preferably each dosage unit contains from about 25 mg to about 100 mg of the salt calculated as the free base.

The compositions can be used by administering them to patients suffering from conditions where reduction of gastric acid secretion is likely to be beneficial, for example patients suffering from or susceptible to duodenal or benign gastric ulceration.

Thus the invention also provides a method of blocking histamine $H_2$-receptors which comprises administering to a patient an effective amount to block said receptors of 2-[2-(5-methyl-4-imidazolylmethylthio)ethylamino]-5-[5-(1,3-benzodioxolyl)methyl]-4-pyrimidone di(methanesulphonate). Typical doses of 25 mg to 100 mg can be administered by intravenous injection, or doses of up to 400 mg can be administered by intravenous infusion up to a combined daily dose of about 1000-1500 mg of the active compound (calculated as the free base).

The following Examples are given by way of illustration of the invention.

EXAMPLES

Example 1

A solution of methanesulphonic acid (8.94 g) in water (90 ml) was heated to 60° C. 2-[2-(5-Methyl-4-imidazolylmethylthio)ethylamino]-5-[5-(1,3-benzodioxolyl)methyl]-4-pyrimidone (18.2 g; prepared from the dihydrochloride by basification with 50% w/v sodium hydroxide solution of an aqueous methanolic solution (50:50 v/v) of the dihydrochloride and crystallisation) was added to the heated solution. The resultant mixture was stirred for 15 minutes and then cooled to 10° C. The cooled mixture was stirred for 30 minutes, and then filtered. Water was removed from the filtrate by distillation with propan-1-ol, and the product was crystallised from propan-1-ol to give 2-[2-(5-methyl-4-imidazolylmethylthio)-ethylamino]-5-[5-(1,3-benzodioxolyl)methyl]-4-pyrimidone di(methanesulphonate) (m.p. 174°-177° C.).

Example 2

2-[2-(5-Methyl-4-imidazolylmethylthio)ethylamino]-5-[5-(1,3-benzodioxolyl)methyl]-4-pyrimidone di(methanesulphonate) (37.5 g) was dissolved in freshly distilled water (1.5 l). The solution was filtered through a prefilter and a membrane filter (0.8 μm pore diameter). The solution was purged of oxygen by flushing with oxygen-free nitrogen for 30 min. The purged solution was filled into ampoules under particle free conditions through a membrane filter (0.2 μm pore diameter). The headspace was purged with oxygen-free nitrogen and the ampoules sealed. The sealed ampoules were sterilized by autoclaving at 121° C. for 20 min.

Comparative Experiment 1

10% w/v solutions, calculated as the free base, were prepared of 2-[2-(5-methyl-4-imidazolylmethylthio)ethylamino]-5-[5-(1,3-benzodioxolyl)methyl]-4-pyrimidone di(methanesulphonate) and of the corresponding dihydrochloride. Samples of each solution were stored at 4° C. and at room temperature (approximately 20° C.) for four weeks.

After this time, neither sample of the solution of the dimethanesulphonate showed signs of precipitation whereas both samples of the solution of the dihydrochloride contained a solid white flocculant mass.

Comparative Experiment 2

5% w/v solutions, calculated as the free base, were prepared of 2-[2-(5-methyl-4-imidazolylmethylthio)ethylamino]-5-[5-(1,3-benzodioxolyl)methyl]-4-pyrimidone di(methanesulphonate) and of the corresponding dihydrochloride. After four weeks at room temperature (approximately 20° C.), no precipitate had formed in the solution of the dimethanesulphonate whereas a fluffy white precipitate had formed in the solution of the dihydrochloride.

We claim:

1. 2-[2-(5-Methyl-4-imidazolylmethylthio)ethylamino]-5-[5-(1,3-benzodioxolyl)methyl]-4-pyrimidone di(methanesulphonate).

2. A pharmaceutical composition having histamine $H_2$-antagonist activity comprising an effective amount of the compound according to claim 1 and a pharmaceutically acceptable carrier.

3. A composition according to claim 2 suitable for parenteral administration.

4. A composition according to claim 3 where the carrier is sterile pyrogen-free water.

5. A composition according to claim 4, containing 2-[2-(5-methyl-4-imidazolylmethylthio)ethylamino]-5-[5-(1,3-benzodioxolyl)methyl]-4-pyrimidone di(methanesulphonate) in an amount of from 5 to 10% w/v calculated as the free base.

6. A composition according to claim 2 in dosage unit form.

7. A method of blocking histamine $H_2$-receptors which comprises administering to a patient an effective amount to block said receptors of the compound according to claim 1.

* * * * *

UNITED STATES PATENT AND TRADEMARK OFFICE
CERTIFICATE OF CORRECTION

PATENT NO. : 4,450,161
DATED : May 22, 1984
INVENTOR(S) : George R. White

It is certified that error appears in the above—identified patent and that said Letters Patent is hereby corrected as shown below:

On the first page of the patent, in the left-hand column, following item [22] insert:

--[30]  Foreign Application Priority Data

May 30, 1981  United Kingdom  8116615 --.

Signed and Sealed this

Twenty-third Day of October 1984

[SEAL]

Attest:

GERALD J. MOSSINGHOFF

Attesting Officer

Commissioner of Patents and Trademarks